US008353814B2

(12) United States Patent
Villafana et al.

(10) Patent No.: US 8,353,814 B2
(45) Date of Patent: Jan. 15, 2013

(54) APPARATUS AND METHOD FOR MOUNTING AN EXTERNAL SCAFFOLD TO A VASCULAR GRAFT

(75) Inventors: Manuel A. Villafana, Minneapolis, MN (US); Eric E. Solien, Lino Lakes, MN (US); Michael P. Winegar, Maple Grove, MN (US); Michael J. Urick, Chaska, MN (US)

(73) Assignee: Kips Bay Medical, Inc., Minneapolis, MN (US)

( * ) Notice: Subject to any disclaimer, the term of this patent is extended or adjusted under 35 U.S.C. 154(b) by 1104 days.

(21) Appl. No.: 12/248,233

(22) Filed: Oct. 9, 2008

(65) Prior Publication Data

US 2010/0160718 A1     Jun. 24, 2010

(51) Int. Cl.
    *A61F 2/04*     (2006.01)
(52) U.S. Cl. .......................................... 600/36; 623/1.13

(58) Field of Classification Search .................... 600/36; 623/1, 11, 12, 1.5, 1.1–1.3; 606/151
See application file for complete search history.

(56) References Cited

U.S. PATENT DOCUMENTS

| 3,626,947 | A | * | 12/1971 | Sparks | 623/1.15 |
| 4,743,251 | A | | 5/1988 | Barra | |
| 5,645,581 | A | * | 7/1997 | Zurbrugg | 623/1.53 |
| 2005/0070995 | A1 | * | 3/2005 | Zilla et al. | 623/1.32 |

* cited by examiner

*Primary Examiner* — Charles A Marmor, II
*Assistant Examiner* — Carrie R Dorna
(74) *Attorney, Agent, or Firm* — Haugen Law Firm PLLP

(57) ABSTRACT

A method for securing a compliant scaffold to an outer surface of a vascular graft includes positioning the scaffold radially about an elongated support tube which includes first and second radially outwardly flared end portions respectively defining first and second open ends of the support tube. The method further includes pulling the vascular graft through a lumen of the support tube, and axially deploying the scaffold over the first end portion of the support tube and into compliant contact with the outer surface of the vascular graft.

17 Claims, 5 Drawing Sheets

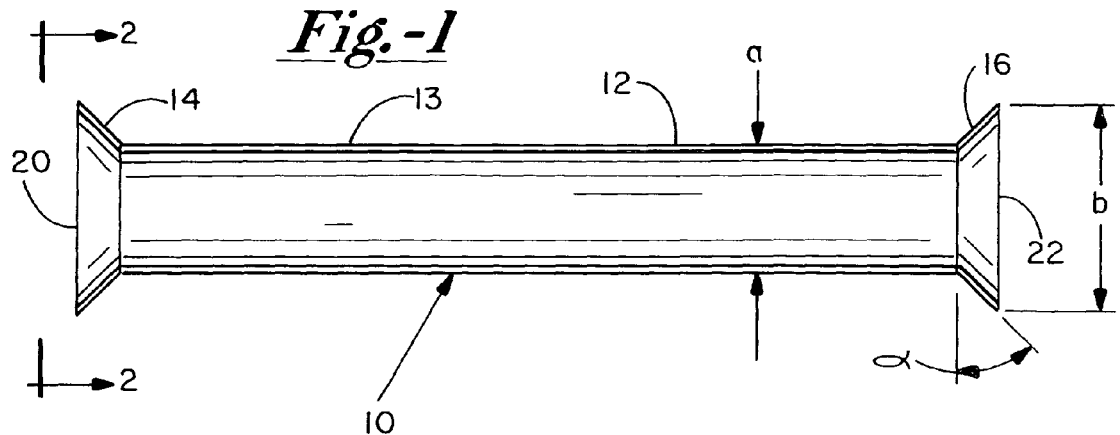
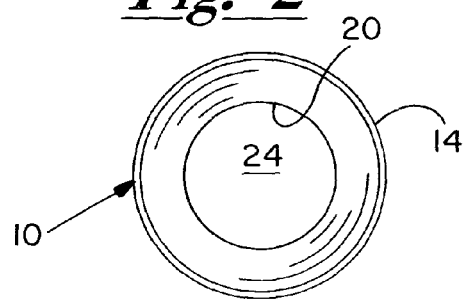
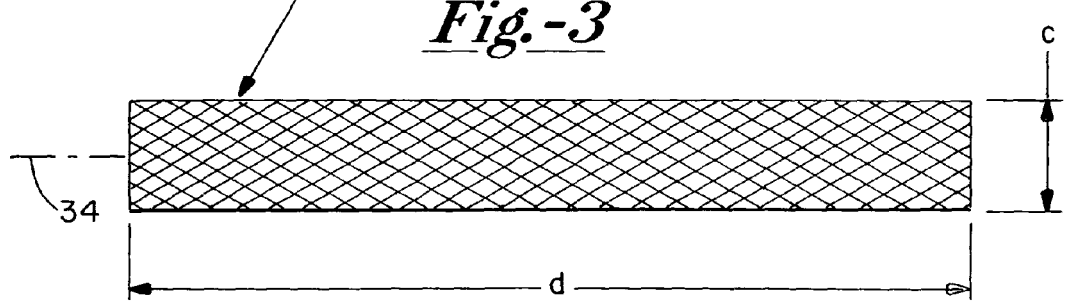
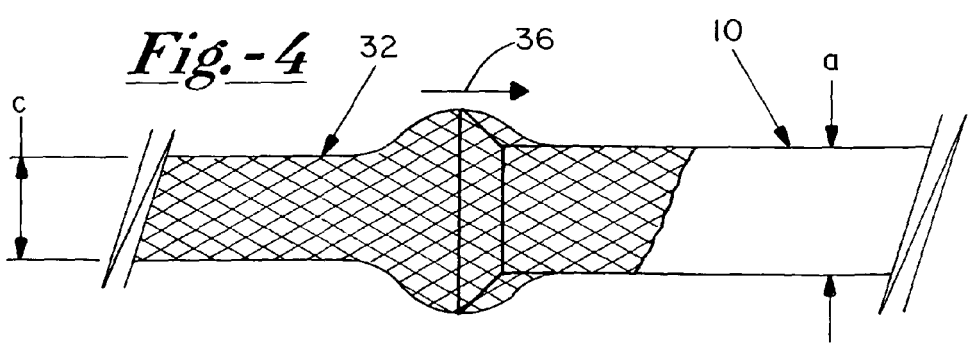

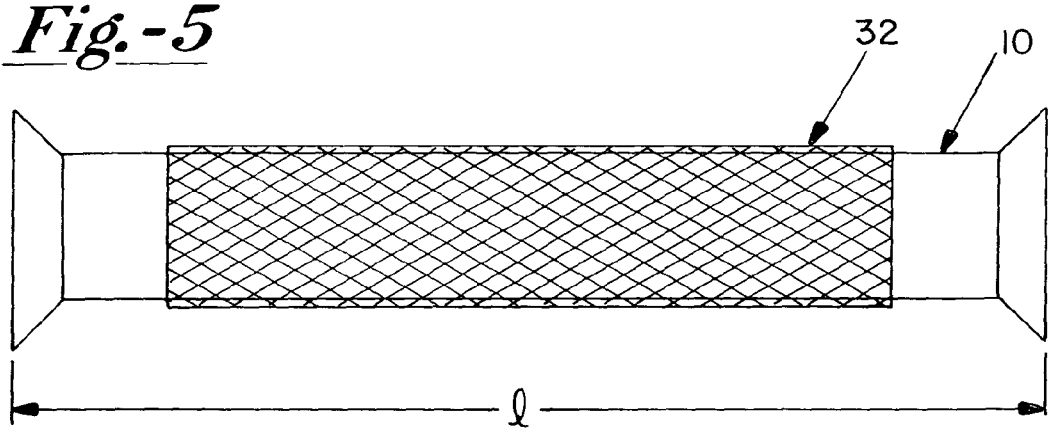
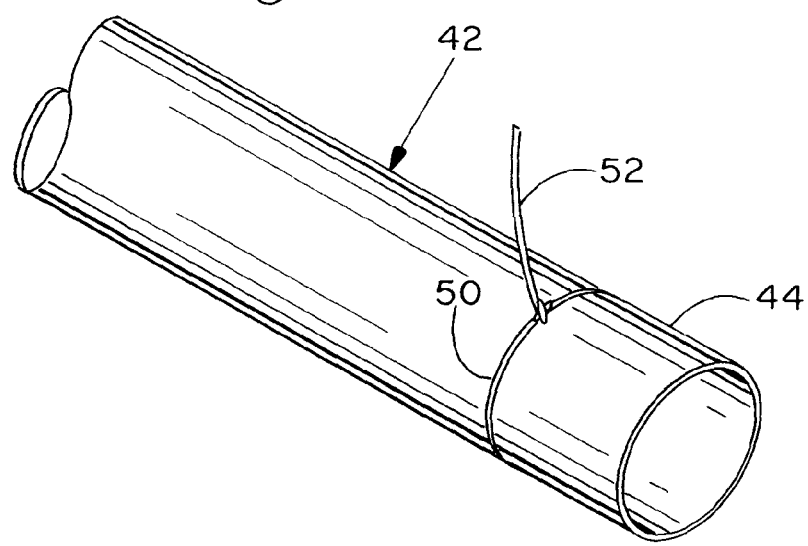
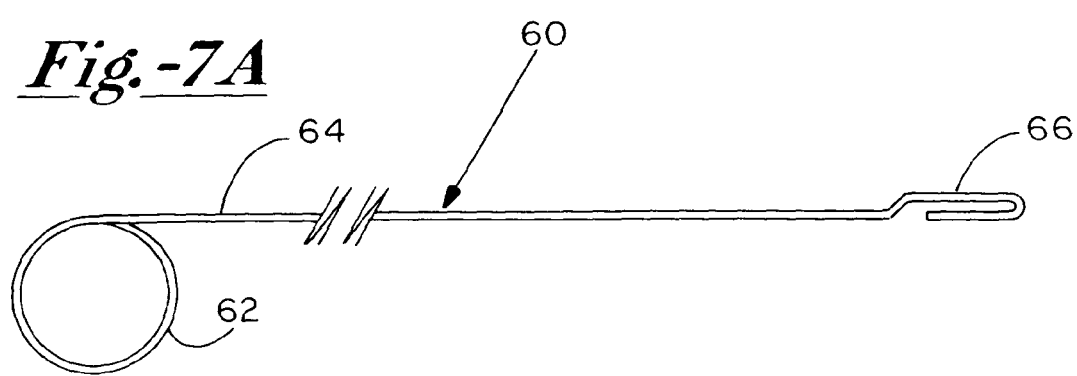

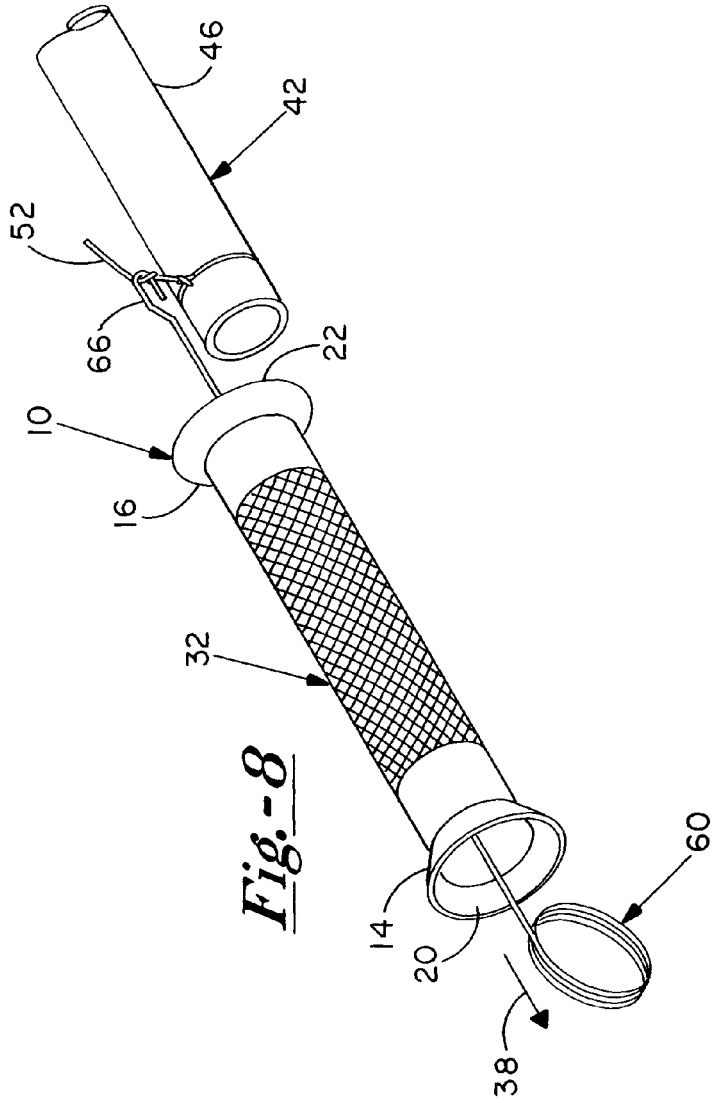
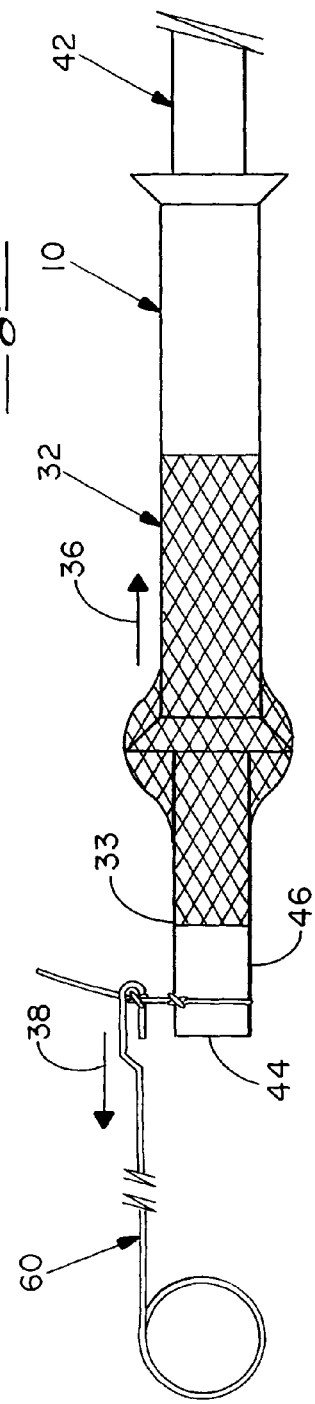

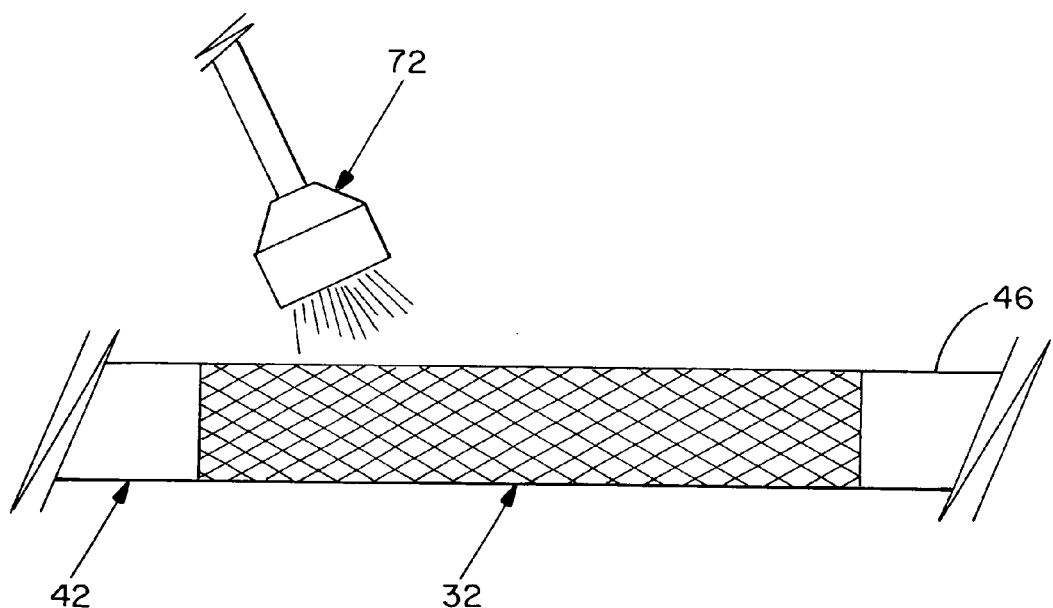

APPARATUS AND METHOD FOR MOUNTING AN EXTERNAL SCAFFOLD TO A VASCULAR GRAFT

FIELD OF THE INVENTION

The present invention relates to surgical implant preparation procedures, generally, and more particularly to an apparatus and procedure for securing a compliant scaffold to an exterior surface of a vascular graft.

BACKGROUND OF THE INVENTION

Vascular grafts of various types are known and find many applications in replacing or providing detours about native blood conduits. Example vascular grafts include synthetic grafts commonly made from expanded polytetrafluoroethylene (e-PTFE), polyethylene terephthalate (PET) or Dacron®. Another common type of vascular grafts involve autologous saphenous vein grafts. Because the patency rates of both such types of vascular grafts are relatively low, numerous studies have been undertaken to find solutions for increasing graft patency.

One solution that appears to have promise in substantially increasing graft patency is described in, for example, U.S. patent application Ser. Nos. 10/834,360, 10/987,313, and 11/797,648, which are owned by the assignee of the present application, and which are herein incorporated by reference in their entirety. Such solution involves a generally tubular scaffold externally supporting the graft segment. In particular, the tubular support is compliant to an extent that the tubular support is capable of resilient radial expansion in a manner mimicking the compliance properties of an artery. The tubular support may be formed of a knitted or woven mesh that is so formed as to exhibit the needed compliance properties.

A challenge in implementing such a tubular support is in mounting or otherwise securing the tubular support scaffold to the graft segment, and, in one embodiment, to an external surface of the vascular graft. Conventional approaches typically involve a cylindrical "straw" or support tube about which the scaffold is positioned. The first end of the vascular graft is then grasped with a clamp, such as a biopsy forceps, and is thereafter pulled through the straw lumen. As the vascular graft emerges from an opposite opening of the straw, the scaffold is removed from the straw and placed into contact with the vascular graft. Typically, a series of sutures may be required to secure the scaffold to the vascular graft.

The conventional process described above, however, has its drawbacks. For example, conventional "straws" are difficult to diametrically size commensurate with the external support device, in that the straw outer diameter must be sufficiently large to temporarily frictionally retain the external support thereat without damage to the external support, while still facilitating ease of removal of the external support therefrom in the deployment process. Moreover, the use of clamps, such as biopsy forceps, directly upon the graft can cause damage thereto.

Consequently, it is a principal object of the present invention to provide an apparatus and method for efficiently securing an external support to a vascular graft while minimizing risk of damage to such graft.

It is a further object of the present invention to provide an apparatus and method for securing a compliant external support to a vascular graft, which apparatus and method significantly simplifies the mounting process.

SUMMARY OF THE INVENTION

By means of the present invention, securement of a resiliently compliant external support to a vascular graft is facilitated. The invention provides a unique preparation apparatus and method which enables efficient handling of a resiliently compliant external support in the vascular graft implant preparation process.

In one embodiment, a support tube for use in securing a compliant scaffold to an outer surface of a vascular graft includes a cylindrical main body portion having a first outer diameter that is between about 80 and 100% of an unstressed inner diameter of the compliant scaffold, and first and second radially outwardly flared end portions respectively defining first and second open ends. The first and second end portions extend from the first outer diameter at the main body portion to a second outer diameter at the first and second open ends, with the second outer diameter being between about 125% and 175% of said first outer diameter dimension. The first and second radially outwardly flared end portions have a flare angle of between about 30° and 60°.

In another embodiment, a method for securing a compliant scaffold to an outer surface of a vascular graft includes positioning the scaffold radially about an elongated support tube, wherein the support tube has a main body portion with a first outer diameter, and first and second radially outwardly flared end portions respectively defining first and second open ends of the support tube. The method further includes ligating a first terminus of the vascular graft with a suture tie, and inserting a suture puller along a first axial direction into the first open end and through a lumen of the support tube. A grasping end of the suture puller is coupled to the suture tie and subsequently retracted along a second axial direction through the support tube lumen and out from the first open end, thereby pulling the first terminus of the vascular graft through the support tube lumen. The scaffold is then axially deployed over the first end portion and into compliant contact with the outer surface of the vascular graft and secured in a location of the vascular graft at or adjacent to the first terminus. The scaffold is removed from the support tube by axially displacing the support tube along a first axial direction with respect to the scaffold.

BRIEF DESCRIPTION OF THE DRAWINGS

FIG. 1 is a side view of a support tube of the present invention;

FIG. 2 is an end view of the support tube illustrated in FIG. 1 along cut line 2-2;

FIG. 3 is a side view of a compliant scaffold of the present invention;

FIG. 4 is a schematic view of the scaffold illustrated in FIG. 3 being externally mounted upon the support tube illustrated in FIGS. 1 and 2;

FIG. 5 is a side view of the scaffold illustrated in FIG. 3 radially secured to the support tube illustrated in FIGS. 1 and 2;

FIG. 6 illustrates a vascular graft with a suture tie;

FIG. 7A is a side view of a suture puller device of the present invention;

FIG. 8 is a schematic of an apparatus of the present invention;

FIG. 9 is a further schematic of the apparatus of the present invention; and

FIG. 10 is a schematic of a combination vascular graft/external support undergoing a sealing process.

DETAILED DESCRIPTION OF THE PREFERRED EMBODIMENTS

Figure 7B:
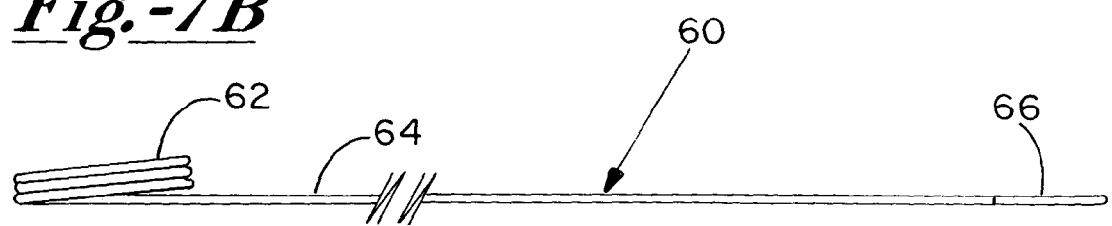
FIG. 7B is a top view of the suture puller device illustrated in FIG. 7A.

The objects and advantages enumerated above together with other objects, features, and advances represented by the present invention will now be presented in terms of detailed embodiments described with reference to the attached drawing figures which are intended to be representative of various possible embodiments of the invention. Other embodiments and aspects of the invention are recognized as being within the grasp of those having ordinary skill in the art.

With reference now to the drawing figures, and first to FIG. 1, a support tube 10 includes a cylindrical main body portion 12 and first and second radially outwardly flared end portions 14,16. Each of first and second end portions 14, 16 respectively define first and second open ends 20,22 of lumen 24.

Main body portion 12 has a first outer diameter "a", and first and second end portions 14, 16 extend from main body portion 12 to a second outer diameter "b" at first and second open ends 20, 22. In some embodiments, second outer diameter dimension "b" is between about 125% and about 175% of first diameter dimension "a". Diametrical differences between first and second outer diameters a, b, however, are also contemplated as being potentially useful in support tube 10 of the present invention. In some exemplary embodiments, first outer diameter dimension "a" may be between about 0.1 and about 0.2 inches, depending upon the intended application for support tube 10.

An example compliant scaffold, such as that described in the above-referenced applications, is illustrated in FIG. 3, wherein scaffold 32 may be a flexible, resilient, and generally tubular external support device, which may be in contact with, for example, an ablumenal surface of a vascular graft segment. In one embodiment, compliant scaffold 32 may take the form of a fiber mesh, such as a knitted, braided, or woven mesh that is made of an alloy or polymer material which, in the desired configuration, provides the required resilience and compliance. In some embodiments, scaffold 32 may be resiliently flexible both axially and radially about longitudinal axis 34. In other embodiments, scaffold 32 may be resiliently compliant only radially about axis 34.

Due to its resilient and flexible characteristics, scaffold 32 has unstressed base dimensions that may be resiliently enlarged upon application of an appropriate force to scaffold 32. As illustrated in FIG. 3, scaffold 32 has an unstressed inner diameter "c" that can be radially enlarged upon the imposition of a radial expansion force to scaffold 32. In addition, scaffold 32 has an unstressed length "d" that may be resiliently enlarged upon the imposition of an axial expansion force to scaffold 32.

As illustrated in FIG. 4, scaffold 32 may be positioned radially about support tube 10 by sliding scaffold 32 along first axial direction 36 over first end portion 14 of support tube 10. Because of its resilient flexibility characteristics, scaffold 32 may resiliently radially expand from unstressed inner diameter "c" to a radial dimension beyond second outer diameter "b" of support tube 10, and then resiliently radially contract against an outer surface 13 of main body portion 12. When fully removably installed upon support tube 10, as illustrated in FIG. 5, scaffold 32 assumes an inner diameter that is substantially equal to first outer diameter "a". In some embodiments, first outer diameter dimension "a" is between about 80 and about 100% of unstressed inner diameter "c" of scaffold 32. Applicants have determined that the relative diameter dimension ranges described above are desirable in generating restorative resilient forces in scaffold 32 which facilitate removable retention of scaffold 32 at main body portion 12 of support tube 10. Relative dimensions of first outer diameter dimension "a" substantially outside of the ranges described above typically generate inadequate or excessive restorative resilient forces in scaffold 32. For example, a first outer diameter dimension "a" that is too large relative to unstressed inner diameter "c" of scaffold 32 will tend to bind scaffold 32 upon main body portion 12 of support tube 10, thereby frustrating removal of scaffold 32 from support tube 10 during the process of deploying scaffold 32 to the vascular graft. Conversely, a first outer diameter dimension "a" that is too small may fail to removably maintain scaffold 32 in place at main body portion 12, as illustrated in FIG. 5.

Support tube 10 of the present invention may be fabricated from a variety of materials capable of providing the functionality described herein. In one embodiment, support tube 10 may be fabricated from a fluorinated polymer such as FEP. Applicants have determined that certain fluoropolymers, such as FEP, Teflon®, and the like provide low surface friction characteristics for support tube 10, wherein scaffold 32 may be installed and removed from a position about support tube 10 with little frictional resistance. The relatively low surface friction characteristics of the selected materials aid in limiting the potential for damage to scaffold 32 in the installment and removal process.

In some embodiments, support tube 10 may be provided in a number of distinct sizes including a plurality of dimensions for first outer diameter dimension "a". Different sizes of support tube 10 may be identified through indicia or other identifying mechanisms. An example identifying mechanism includes distinct colorants added to the material of support tube 10, wherein each color is associated with a known first outer diameter dimension "a". Such association enables apparatus operators to quickly determine an appropriately-sized support tube 10 in connection with a particular scaffold 32 being used.

With reference back to FIG. 1, first and second end portions 14, 16 are preferably radially outwardly flared, as described above. Such a flared configuration further aids in removably retaining scaffold 32 at main body portion 12 of support tube 10. While a variety of flare angles and lengths are contemplated as being useful in support tube 10, one embodiment of the present invention includes a flare angle "α" of between about 30 degrees and about 60 degrees.

In order to secure scaffold 32 to a vascular graft 42, the vascular graft is first measured to determine the appropriate scaffold diameter dimension, as described above. Vascular graft 42 may be an autologous or homologous vein, or may be an artificial vascular prosthesis of conventional type. To prepare vascular graft 42, a first terminus 44 is ligated with a suture tie 50. In some embodiments a tail 52 of suture tie 50 is left, wherein tail 52 may be at least about 30 cm in length. The operator may grasp suture tail 52 in pulling vascular graft 42 through lumen 24 of support tube 10.

Figure 7C:
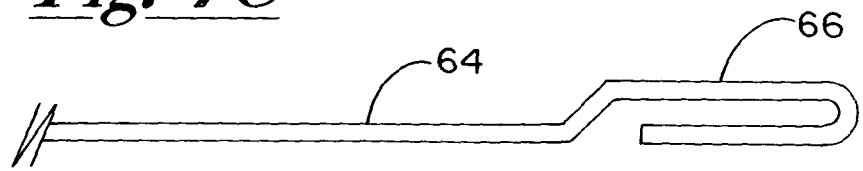
FIG. 7C is a portion of the suture puller device illustrated in FIGS. 7A and 7B.

Applicants have determined that a useful tool in grasping vascular graft 42 is a suture puller device 60, as illustrated in FIGS. 7A-7C. Suture puller 60 includes a handle 62, a stem 64, and a grasping end 66. Stem 64 of suture puller 60 may be sized and configured to operably extend through lumen 24 of support tube 10, and is preferably longer than the total length "L" of support tube 10. In this fashion, grasping end 66 may be coupled to suture tail 52 axially beyond second open end 22 of support tube 10, while handle 62 remains axially outside of first open end 20. In the illustrated embodiment, suture puller 60 may be a formed 22 AWG wire of stainless steel having a first looped portion forming handle 62, and a second hooked portion forming grasping end 66. A variety of suture puller devices of various size and material are commercially available. An example commercial source for suture puller devices is Medtronic, Inc.

As illustrated in FIG. 8, suture puller 60 may be operably positioned through lumen 24 of support tube 10 in order to couple to suture tail 52. Once coupled, suture puller 60 is withdrawn along second axial direction 38 through lumen 24 and out from first open end 20 of support tube 10, thereby pulling first terminus 44 of vascular graft 42 through support tube lumen 24. In some embodiments, vascular graft 42 may be wetted with heparinized saline to reduce frictional resistance in drawing vascular graft 42 through lumen 24.

As first terminus 44 of vascular graft 42 emerges from first open end 20 of support tube 10, scaffold 32 is deployed along second axial direction 38 over first end portion 14 and into compliant contact with outer surface 46 of vascular graft 42. This deployment process is illustrated in FIG. 9. Scaffold 32 may be secured to vascular graft 42 by one or more sutures at first end 33 of scaffold 32. Such suture may be placed at or adjacent to first terminus 44. Once such securement is made, the remainder of scaffold 32 is deployed upon outer surface 46 of vascular graft 42 by axially displacing support tube 10 along first axial direction 36 relative to scaffold 32. Manual assistance in removing scaffold 32 from support tube 10 may also be required.

Once scaffold 32 is fully deployed upon outer surface 46 of vascular graft 42, an adhering sealant, such as fibrin, is applied to the interface between scaffold 32 and vascular graft 42. In one embodiment, the sealant may be applied to the graft/scaffold combination through a spray mechanism 72. While the sealant fibrin is a preferred adhering sealant material, it is contemplated that other sealant materials may be utilized in ensuring securement of scaffold 32 to vascular graft 42. In some embodiments, vascular graft 42 may be radially inflated against scaffold 32 prior to the sealant spray application process. Such inflation further ensures sealing contact between scaffold 32 and outer surface 46 of vascular graft 42.

Respective ends of the apparatus illustrated in FIG. 10 may be trimmed to ensure appropriate angles and consistent cut edges for coronary anastomosis. As described in the above-referenced applications, scaffold 32 may be sized to constrict the natural diameter of vascular graft 42, and particularly in applications involving vein grafts for coronary bypass procedures.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications may be accomplished without departing from the scope of the invention itself.

What is claimed is:

1. A method for securing a compliant scaffold to an outer surface of a vascular graft, said method comprising:
   (a) positioning said scaffold radially about an elongated support tube, said support tube having a main body portion with a first outer diameter, and first and second radially outwardly flared end portions respectively defining first and second open ends of said support tube;
   (b) ligating a first terminus of said vascular graft with a suture tie;
   (c) inserting a suture puller along a first axial direction into said first open end and through a lumen of said support tube;
   (d) coupling a grasping end of said suture puller to said suture tie;
   (e) retracting said suture puller along a second axial direction through said support tube lumen and out from said first open end, thereby pulling said first terminus of said vascular graft through said support tube lumen;
   (f) axially deploying said scaffold over said first radially outwardly flared end portion and into compliant contact with said outer surface of said vascular graft;
   (g) securing said scaffold to a location of said vascular graft at or adjacent to said first terminus; and
   (h) removing said scaffold from said support tube by axially displacing said support tube along said first axial direction with respect to said scaffold.

2. A method as in claim 1, including, following step (h), applying a sealant to said scaffold.

3. A method as in claim 2, wherein said sealant is fibrin.

4. A method as in claim 1 wherein, following step (h), said vascular graft is radially inflated against said scaffold.

5. A method as in claim 1 wherein said support tube is fabricated from a fluorinated polymer.

6. A method as in claim 1 wherein said first outer diameter of said support tube is between about 0.1 and about 0.2 inches.

7. A method for securing a scaffold to an outer surface of a vascular graft, said method comprising:
   (a) providing a support tube having first and second open ends and a main body portion with a first outer diameter, said support tube including a guide portion extending radially outwardly from said main body portion at or adjacent to said first open end;
   (b) positioning said scaffold circumaxially about said main body portion of said support tube;
   (c) positioning the vascular graft within a lumen of said support tube, with a first terminus of the vascular graft protruding from said first open end of said support tube;
   (d) axially deploying a first end of said scaffold in a first axial direction over said guide portion and into contact with the outer surface of the vascular graft;
   (e) securing the first end of the scaffold to a location of the vascular graft at or adjacent to the first terminus; and
   (f) removing a remainder of the scaffold from said support tube by axially displacing said support tube with respect to the scaffold along a second axial direction opposite said first axial direction.

8. A method as in claim 7 wherein said guide portion is frusto-conically configured, arranged with an increasing diameter toward said first open end, and terminating in a first termination diameter.

9. A method as in claim 8 wherein said termination diameter is between about 125% and 175% of said first outer diameter.

10. A method as in claim 7 wherein said support tube includes a second guide portion extending radially outwardly from said main body portion at or adjacent to said second open end.

11. A method as in claim 10, including positioning the scaffold between the said first and second guide portions.

12. An apparatus for reinforcing an outer surface of a vascular graft, said apparatus comprising:

a support tube having first and second open ends and a main body portion with a first outer diameter, said support tube including a guide portion extending radially outwardly from said main body portion at or adjacent to said first open end;

a radially resilient generally tubular scaffold for compliant contact with the outer surface of the vascular graft, said scaffold having a first inner diameter when in an unstressed condition, wherein said first inner diameter is equal to or greater than said first outer diameter of said support tube, said scaffold being capable of resiliently radially expanding over said guide portion from a position circumaxially about said main body portion of said support tube to resiliently engage with the outer surface of the vascular graft.

13. An apparatus as in claim 12 wherein said guide portion is frusto-conically configured, and arranged with increasing diameter toward said first open end, and terminating in a termination diameter.

14. An apparatus as in claim 13 wherein said termination diameter is between about 125% and 175% of said first outer diameter.

15. An apparatus as in claim 12 wherein said guide portion includes a flare angle of between about 30° and 60°.

16. An apparatus as in claim 12 wherein said support tube includes a second guide portion extending radially outwardly from said main body portion at or adjacent to said second open end.

17. An apparatus as in claim 16 wherein said radially resilient scaffold is positioned between said first and second guide portions of said support tube.

* * * * *

UNITED STATES PATENT AND TRADEMARK OFFICE
CERTIFICATE OF CORRECTION

PATENT NO. : 8,353,814 B2
APPLICATION NO. : 12/248233
DATED : January 15, 2013
INVENTOR(S) : Villafana et al.

Page 1 of 1

It is certified that error appears in the above-identified patent and that said Letters Patent is hereby corrected as shown below:

Column 4, line 49, replace "the present invention includes a flare angle "a" of between" with -- the present invention includes a flare angle "α" of between --

Signed and Sealed this
Nineteenth Day of March, 2013

Teresa Stanek Rea
*Acting Director of the United States Patent and Trademark Office*